(12) United States Patent
Guo et al.

(10) Patent No.: US 10,624,336 B2
(45) Date of Patent: Apr. 21, 2020

(54) IN-VITRO EMBRYONIC CULTURE MEDIUM COMPRISING AN INHIBITOR OF CATHEPSIN L AND THE USE OF THE SAME IN EMBRYO CRYOPRESERVATION

(71) Applicant: BEIJING UNIVERSITY OF AGRICULTURE, Beijing (CN)

(72) Inventors: Yong Guo, Beijing (CN); Hemin Ni, Beijing (CN); Yu Chen, Beijing (CN); Di Liu, Beijing (CN); Xiangguo Wang, Beijing (CN); Xiaolong Qi, Beijing (CN)

(73) Assignee: BEIJING UNIVERSITY OF AGRICULTURE, Beijing (CN)

( * ) Notice: Subject to any disclaimer, the term of this patent is extended or adjusted under 35 U.S.C. 154(b) by 92 days.

(21) Appl. No.: 15/832,915

(22) Filed: Dec. 6, 2017

(65) Prior Publication Data
US 2018/0160677 A1    Jun. 14, 2018

(30) Foreign Application Priority Data

Dec. 13, 2016  (CN) .......................... 2016 1 1144294

(51) Int. Cl.
*A01N 1/02*   (2006.01)
*C12N 5/073*  (2010.01)

(52) U.S. Cl.
CPC ......... *A01N 1/0221* (2013.01); *C12N 5/0604* (2013.01); *C12N 2501/70* (2013.01); *C12N 2501/734* (2013.01); *C12N 2501/999* (2013.01)

(58) Field of Classification Search
CPC ................ A01N 1/0221; C12N 5/0604; C12N 2501/70; C12N 2501/999; C12N 2501/734
See application file for complete search history.

(56) References Cited

FOREIGN PATENT DOCUMENTS

| CN | 102250832 A | 11/2011 |
| CN | 103710299 A | 4/2014 |
| CN | 104278011 A | 1/2015 |

OTHER PUBLICATIONS

Kim et al. Inhibition of cathepsin B activity reduces apoptosis by preventing cytochrome c release from mitochondria in porcine parthenotes. J. Reprod. Dev. 61: 261-268, 2015 (Year: 2015).*
Tsukamoto et al. Functional analysis of lysosomes during mouse preimplantation embryo development. J. Reprod. Dev. 59: 33-39, 2013 (Year: 2013).*
Stroh et al. The role of caspases in cryoinjury: caspase inhibition strongly improves the recovery of cryopreserved hematopoietic and other cells. The FASEB Journal express article. Published online Aug. 7, 2002. p. 1-16 (Year: 2002).*
Cao et al. Effects of chemically defined medium on early development of porcine embryos derived from parthenogenetic activation and cloning. Abstract only. Zygote. Aug. 2012;20(3):229-36 (Year: 2012).*
Chatot et al. An improved culture medium supports development of random-bred 1-cell mouse embryos in vitro. J. Reprod. Fert. 86, 679-688 (Year: 1989).*
Liu, et al. "The Effect of Cathepsin on in vitro Developmental Capacity of Oocytes from Adult Sheep", Acta Veterinaria et Zootechnica Sinica 2011,42(12):1704-1711.
Search Report was dated Jan. 26, 2019 by the SIPO for CN Application No. 201611144294.0, which was filed on Dec. 13, 2016 and published as CN 106479962 A on Mar. 8, 2017 (Applicant—Beijing University of Agriculture) (Original-3 pages).
First Office Action was dated Feb. 2, 2019 by the SIPO for CN Application No. 201611144294.0, which was filed on Dec. 13, 2016 and published as CN 106479962 A on Mar. 8, 2017 (Applicant—Beijing University of Agriculture) (Original-3 pages).

* cited by examiner

*Primary Examiner* — Taeyoon Kim
(74) *Attorney, Agent, or Firm* — Ballard Spahr LLP

(57) ABSTRACT

The present invention belongs to the technical field of embryo cryopreservation. In particular, the present invention relates to an in-vitro embryonic culture medium for improving the thawed recovery rate of an embryo, comprising an inhibitor of Cathepsin L inhibitor, for example, E-64d. The present invention also relates to a method for improving the freezing resistance and the thawing recovery rate of an embryo and a method for freezing an embryo. With the present invention, the freezing resistance and the thawing recovery rate of an embryo are significantly improved.

13 Claims, No Drawings

IN-VITRO EMBRYONIC CULTURE MEDIUM COMPRISING AN INHIBITOR OF CATHEPSIN L AND THE USE OF THE SAME IN EMBRYO CRYOPRESERVATION

CROSS-REFERENCE TO RELATED APPLICATIONS

This present application claims priority to Chinese patent application serial number 201611144294.0 entitled "AN IN-VITRO EMBRYONIC CULTURE MEDIUM COMPRISING AN INHIBITOR OF CATHEPSIN L AND THE USE OF THE SAME IN EMBRYO CRYOPRESERVATION" filed on Dec. 13, 2016, the disclosure of which is incorporated herein by reference in its entirety.

TECHNICAL FIELD

The present invention belongs to the technical field of embryo cryopreservation. In particular, the present invention relates to the use of an inhibitor of Cathepsin L in embryo cryopreservation.

BACKGROUND

The biological technique related to embryo transfer, in-vitro fertilization, transgenesis, cloning, and the like often involves embryo cryopreservation. It is of great concern on how to better freeze embryos so that the embryos are still able to normally develop after they are thawed.

In prior-art methods of freezing embryos, a cryoprotectant is often employed. The cryoprotectant is added into a freezing solution for the purpose of protecting cells against damage from freezing shock. The cryoprotectants, most of which are small molecules of permeability, protect cells against damage from freezing mainly by penetrating into the cells, where hydration occurs so as to enhance viscosity of intracellular fluid. Different cryoprotectants have different effect of cell cryopreservation due to type, concentration, molecular size, permeability, water activity and mechanism of intracellular action. As the concentration of a cryoprotectant in a freezing solution increases, the amount of the cryoprotectant penetrating into cells increases accordingly. Generally, the cryoprotectant is toxic per se, and it will kill the cells when at an excessively high concentration, while will not serve to protect the cells when at an excessively low concentration.

Moreover, There is also data in the prior art showing that the frozen embryos, upon transfer, have a much more reduced birth rate as compared with the fresh embryos. This suggests that freezing or in vitro treatment with a cryoprotectant has influence on the later development of embryos to some degrees.

Therefore, there is a need in the art for a novel solution for freezing embryos, which can improve the freezing resistance and the thawing recovery rate of embryos. Additionally or alternatively, such solution can also reduce the cryoprotectant amount as used, thereby decreasing the toxic side effect on the embryo and achieving effective embryo freezing.

SUMMARY OF THE INVENTION

An object of the present invention is to provide a novel solution for freezing embryos, which can improve the freezing resistance and the thawing recovery rate of the embryo. Additionally or alternatively, such solution can also reduce the cryoprotectant amount as used, thereby decreasing the toxic side effect on the embryo and achieving effective embryo freezing.

Surprisingly, the present inventors discovered that the freezing resistance and the thawing recovery rate of an embryo could be significantly increased by incubating the embryo in an in-vitro embryonic culture medium containing an inhibitor of Cathepsin L, for example E-64d, for a period of time, and then subject the embryo to freezing, such as programmed freezing. On the basis of this discovery, the present inventors arrived at the following invention.

In a first aspect, the present invention provides an in-vitro embryonic culture medium comprising an inhibitor of Cathepsin L.

In a second aspect, the present invention provides a method for improving the freezing resistance and the thawing recovery rate of an embryo, comprising incubating the embryo in the in-vitro embryonic culture medium according to the first aspect of the present invention, preferably for 1-4 hours and most preferably for 2 hours, prior to the embryo freezing.

In a third aspect, the present invention provides a method for freezing an embryo comprising the steps of: a) incubating the embryo in an in-vitro embryonic culture medium according to the first aspect of the invention for a period of time, preferably for 1-4 hours, and most preferably for 2 hours; and b) subjecting the embryo incubated in step a) to freezing, preferably programmed freezing.

The present inventors applied an inhibitor of Cathepsin L in the field of embryo cryopreservation for the first time, and discovered surprisingly that the freezing resistance and the thawing recovery rate of the embryos can be significantly increased by adding an inhibitor of Cathepsin L to an in-vitro embryonic culture medium and incubating the embryo to be frozen in the in-vitro embryonic culture medium with the inhibitor of Cathepsin L added for a period of time. Additionally or alternatively, the cryoprotectant amount as used in a freezing solution can be reduced by such incubation, and thereby the toxic side effect of the cryoprotectant on the embryo is decreased.

DETAILED DESCRIPTION

The particular technical solutions of the present invention will be described below in a further clear and complete manner. It is to be understood that the technical solutions as particularly described herein are for illustrative purposes only, and are not intended to limit the protection scope of the invention in any way. Modifications may be made to the technical solutions of the present invention without departing from the spirit and principle of the present invention. The protection scope of the present invention is defined by the appended claims.

It will be noted that, as used in this specification and the appended claims, the singular forms "a," "an" and "the" include plural referents unless the content clearly dictates otherwise. Thus, for example, reference to "an embryo" includes one, two, or more embryos. Similarly, reference to a plurality of referents should be interpreted as comprising a single referent and/or a plurality of referents unless the content and/or context clearly dictate otherwise. Thus, reference to "embryos" does not necessarily require a plurality of such embryos. Instead, it will be appreciated that independent of conjugation; one or more embryos are contemplated herein.

As described above, an object of the present invention is to provide a novel solution for freezing embryos, which can improve the freezing resistance and the thawing recovery rate of an embryo. Additionally or alternatively, such solution can also reduce the cryoprotectant amount as used, thereby decreasing the toxic side effect on the embryo and achieving effective embryo freezing.

Surprisingly, the present inventors discovered that the freezing resistance and the thawing recovery rate of an embryo could be significantly increased by incubating the embryo in an in-vitro embryo culture medium comprising an inhibitor of Cathepsin L for a period of time and then subjecting the embryo to freezing, for example, programmed freezing. On the basis of this discovery, the present inventors arrived at the following invention.

In a first aspect, the present invention provides an in-vitro embryonic culture medium comprising an inhibitor of Cathepsin L.

In an embodiment, the inhibitor of Cathepsin L is E-64d, E-64 or Z-Phe-Phe-FMK.

E-64d is an specific inhibitor of Cathepsin L, which is also known as Aloxistatin, and has a chemical name of ethyl (2S,3S)-3-[[(2S)-4-methyl-1-(3-methylbutylamino)-1-oxopentan-2-yl]carbamoyl]oxirane-2-carboxylate. Its molecular weight is 342.43, its molecular formula is $C_{17}H_{30}N_2O_5$, and its chemical structure is shown as below:

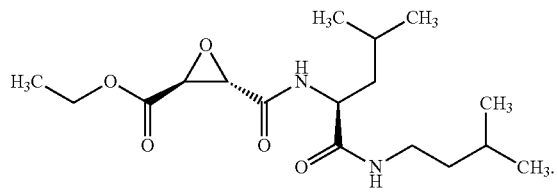 [SMILES: CCOC(=O)[C@H]1O[C@@H]1C(=O)N[C@@H](CC(C)C)C(=O)NCCC(C)C]

E-64 is an irreversible selective inhibitor of cathepsin L, and has a chemical name of (2R,3R)-3-[[(2S)-1-[4-(Diaminomethylideneamino)butylamino]-4-methyl-1-oxopentan-2-yl]carbamoyl]oxirane-2-carboxylic acid. Its molecular weight is 357.41, its molecular formula is $C_{15}H_{27}N_5O_5$, and its chemical structure is shown as below:

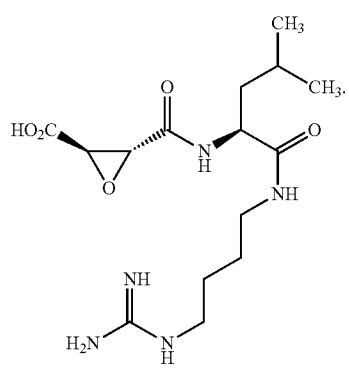 [SMILES: CC(C)C[C@H](NC(=O)[C@@H]1O[C@H]1C(=O)O)C(=O)NCCCCNC(=N)N]

Z-Phe-Phe-FMK is an irreversible permeable inhibitor of Cathepsin L. Its molecular weight is 462.50, its molecular formula is $C_{27}H_{27}FN_2O_4$, and its chemical structure is shown as below:

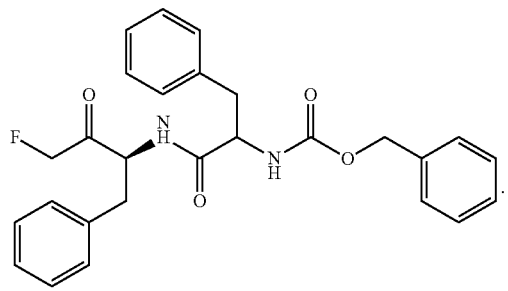 [SMILES: O=C(NC(Cc1ccccc1)C(=O)N[C@@H](Cc1ccccc1)C(=O)CF)OCc1ccccc1]

In a particular embodiment, the inhibitor of Cathepsin L is E-64d. In a further embodiment, E-64d has a concentration of 0.5-3 µmol/L, for example, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9 or 3.0 µmol/L, or any concentration intervals derived from these values, such as 0.5-2 µmol/L or 1.0-1.5 µmol/L, preferably 1.0 µmol/L.

In addition to the above-mentioned inhibitor of Cathepsin L, the in-vitro embryonic culture medium further comprises any medium selected from the group consisting of CZB medium, MTF medium, KSOM medium, $CR_1$ medium, and $CR_2$ medium.

CZB medium is a medium that allows a fertilized embryo of mice from various strains to develop into the blastocyst stage, and is currently widely used in embryonic operations and various mouse cloning experiments.

MTF medium is an embryonic culture medium for preimplantation, which is based on the Krebs-Ring carbonate solution and has simple ingredients. This medium mainly comprises sodium pyruvate, sodium lactate and glucose for providing energy, and serum albumin.

KSOM medium is a medium that is used primarily for culturing an in-vitro fertilized (IVF) mouse embryo or a B6C3F1 mouse oocyte reconstituted after enucleation and electrofusion.

$CR_1$ and $CR_2$ media are those that are used for culturing an embryo at a later stage of development from species such as pigs, cattle, and sheep. The specific formulae are slightly adjusted depending on the particular stage of the embryo.

The embryo is incubated in the in-vitro embryonic culture medium comprising an inhibitor of Cathepsin L according to the first aspect of the present invention for a period of time prior to the embryo freezing, whereby the freezing resistance and the thawing recovery rate of the embryo can be significantly improved, wherein the thawed recovery rate can be improved, for example, by up to 10%.

In a second aspect, the present invention provides a method for improving the freezing resistance and the thawing recovery rate of an embryo, comprising incubating the embryo in the in-vitro embryo culture medium according to the first aspect of the present invention prior to the embryo freezing.

The incubation may take place at 37° C., 5% $CO_2$ and 100% humidity for a suitable period of time, for example, 1-4 hours, such as 1, 2, 3 or 4 hours, and preferably 2 hours.

The embryo may be derived from any species. For example, the embryo may be derived from a mammal such as mouse, rat, pig, cattle, sheep, or primate, for example, human.

The embryo may be at any stage suitable for freezing. For example, the embryo may be at 4-cell to blastocyst stage.

The embryo may be obtained through any means, for example, an in-vivo or in-vitro method. For the embryo obtained through an in-vivo method, for example, it may include a fertilized embryo which has developed into, for example, the 4-cell stage through the blastocyst stage in the maternal body of a non-human mammal after self-breeding or artificial insemination and is obtained through a surgical or non-surgical procedure from said maternal body. The non-human mammal may be, for example, a mouse, rat, pig, cattle, sheep, or primate excluding human. For the embryo obtained through an in-vitro method, it may include a fertilized embryo obtained through in-vitro fertilization, for example, parthenogenetic activation or intracytoplasmic sperm injection, of a mature oocyte. The mature oocyte may be derived from any species, for example, a mammal such as mouse, rat, pig, cattle, sheep, or primate, for example, human.

In a third aspect, the present invention provides a method for freezing an embryo, comprising the steps of incubating the embryo in an in-vitro embryo culture medium according to the first aspect of the present invention; and freezing the incubated embryo.

The incubation may take place at 37° C., 5% $CO_2$ and 100% humidity for a suitable period of time, for example, 1-4 hours, such as 1, 2, 3 or 4 hours, and preferably 2 hours.

The embryo may be derived from any species. For example, the embryo may be derived from a mammal such as a mouse, rat, pig, cattle, sheep, or primate, for example, human.

The embryo may be at any stage suitable for freezing. For example, the embryo may be at 4-cell stage to blastocyst stage.

The embryo may be obtained through any means, for example, an in-vivo or in-vitro method. For the embryo obtained through an in-vivo method, for example, it may include a fertilized embryo which has developed into, for example, the 4-cell stage through the blastocyst stage in the maternal body of a non-human mammal after self-breeding or artificial insemination and is obtained through a surgical or non-surgical procedure from said maternal body. The non-human mammal may be, for example, a mouse, rat, pig, cattle, sheep, or primate excluding human. For the embryo obtained through an in-vitro method, for example, it may include a fertilized embryo obtained through in-vitro fertilization, for example, parthenogenetic activation or intracytoplasmic sperm injection, of a mature oocyte. The mature oocyte may be derived from any species, for example, a mammal such as a mouse, rat, pig, cattle, sheep, or primate, for example, human.

The incubated embryos may be frozen in any suitable means. The method of freezing an embryo employed in the art includes, for example, programmed freezing, rapid freezing, vitrification freezing, and the like.

Programmed freezing mainly comprises gradient dehydration with a cryoprotectant at a low concentration and slow cooling with a control rate freezer. The main operation steps comprise: subjecting an embryo to gradient dehydration by placing the embryo sequentially in a series of solutions comprising a cryoprotectant at a gradually increasing concentration; placing the embryo in a control rate freezer to rapidly cool the embryo to −5 to −7° C. for seeding (formation of artificially induced ice crystals), and then slowly cool the embryo to −30 to −80° C.; and, if desired, storing the embryo in liquid nitrogen.

Vitrification freezing is a method of freezing an embryo as proposed by Rall and Fahy in 1985. The principle underlying vitrification freezing is as follows: the intracellular water is replaced out with a solution comprising a cryoprotectant at a high concentration, and then transformed from the liquid state to the amorphous solid state in glassy shape by rapid cooling. Vitrification freezing involves simple operation steps, which comprise replacing intracellular and extracellular water with a solution comprising a cryoprotectant at a high concentration, rapidly cooling the embryo so as to extremely increase the viscosity of and solidify the solution, and placing the embryo in liquid nitrogen for storage.

One-step freezing method utilizes a cryoprotectant at a high concentration to dehydrate the embryo before freezing, thereby reducing the formation of intracellular ice crystals during freezing. The method is characterized in that the embryo does not need special cooling procedure after it is dehydrated at room temperature and that the freezing process can be completed in a very short period of time. Therefore, this method is of important value in practice.

Programmed freezing is employed in the present invention; however, other methods may also be used. The general procedure for programmed freezing as employed in the present invention is as follows. The embryo is subjected to gradient dehydration with solutions comprising a cryoprotectant at a gradually increasing concentration, and rapidly cool (for example, at 1° C./min) the embryo to −5° C. to −7° C., and then slowly cool (for example, at 0.3° C./min) the embryo to −30° C. to −80° C. Where long-term cryopreservation is required, the embryo can then be placed in liquid nitrogen.

The freezing resistance and the thawing recovery rate of an embryo can be significantly improved by adding an inhibitor of Cathepsin L to an in-vitro embryo culture medium, and incubating the embryo to be frozen in the in-vitro embryo culture medium comprising the inhibitor of Cathepsin L for a period of time. Additionally or alternatively, the cryoprotectant amount as used in the freezing solution can be reduced through the incubation procedure, thereby decreasing the toxic side effect of the cryoprotectant on the embryo.

EXAMPLES

1. Materials
1.1. Main Instruments and Equipments
Pipette: Beijing Baygene Biotech Company (1 mL, 200 µL, 100 µL, and 10 µL)
Medical Centrifuge: Beijing Medical Centrifuge Factory, LDZ4-0.8
$CO_2$ Incubator: Heal Force Company, HF90
Stereoscopic Microscope: Jiangnan Microscope Factory, X11-3
Clean Bench: Shanghai Zhicheng Analytical Instruments Manufacturing Co., Ltd, ZHJH-1112B
Electronic Balance: Beijing Sartorius Instrument System Co., Ltd, BS124S
PH Meter: Thermo Company, 868
Precision Heating Plate: Beida Instruments, MEH-2
Water Bath: Beijing Changan Scientific Instrument Factory, HH.S1-Ni
1.2. Main Reagents
1.2.1 E-64d: Available from Abcam, Catalog #: ab144048, CAS No.: 88321-09-9, PubChem Identification No.: 65663.
1.2.2 CZB Medium
(1) Formula of CZB Stock, 100 mL

|  | g/100 mL |
|---|---|
| Solution A | |
| $KH_2PO_4$ | 0.0161 |
| NaCl | 0.4770 |

-continued

|  | g/100 mL |
|---|---|
| KCl | 0.0361 |
| EDTANa$_2$ | 0.0037 |
| NaHCO$_3$ | 0.2101 |
| Solution B | |
| CaCl$_2$·2H$_2$O | 0.025 |
| MgSO$_4$·7H$_2$O | 0.0291 |

Formulation protocol: Solutions A and B were mixed, and then were made to 100 mL with autoclaved ultrapure water.
(2) Formula of CZB Working Solution, 5 mL

| CZB stock | 5 mL |
|---|---|
| Glucose | 0.005 g |
| Bovine serum albumin (BSA) (9647) | 0.025 g |
| Sodium pyruvate (0.25M) | 6 µL |
| Glutamine (0.2M) | 25 µL |
| Sodium lactate (2M) | 78.3 µL |

1.2.3. E-64d-Containing In-Vitro Embryo Culture Medium (Referred to as E-64d-CZB Working Solution Hereinafter)

E-64d was dissolved in a small amount of DMSO and then added to the CZB working solution to give final E-64d concentrations of 0.5, 1, 1.5, 2, 3, 5, and 10 µmol/L. The in-vitro embryo culture medium was stored at 4° C.

1.3. Test Materials

In this study, sexually mature ICR mice aged 8-12 weeks and weighed about 28 g were used. The mice were purchased from Beijing Vital River Laboratory Animal Technology Co., Ltd.

2. Methods 2.1. Harvest and Collection of Normally Hatched Blastocysts from Mice Female mice with pale pink vulvas were randomized and intraperitoneally injected with pregnant mare serum gonadotrophin (PMSG) at a dosage of 10 IU/mouse. After 48 hours, the female mice were further injected with human chorionic gonadotropin (hCG) at a dosage of 10 IU/mouse, and then were immediately housed in a cage with adult male mice at a ratio of 1:1 overnight for mating. The mice were checked for mating at 8 a.m. next day and injected with anti-PMSG (A-PMSG) at a dosage of 10 IU/mouse once the vaginal suppository was observed. The mice were sacrificed at 9 a.m. on Day 5 after the vaginal suppository was observed. The uteruses on both sides of the mice were removed and flushed with the PBS working solution to obtain normally hatched blastocysts.

2.2. Freezing of Normally Hatched Blastocysts from Mice

The normally hatched blastocysts as obtained (about 100 blastocysts) were rinsed with 100 µl PBS solution for three times and then with 100 µl CZB working solution for another three times. Afterwards, the blastocysts were transferred into drops of the E-64d-CZB working solutions at 0, 0.5, 1, 1.5, 2, 3, 5, and 10 µmol/L, and then incubated in vitro in an incubator at 37° C., 5% CO$_2$ in air, and 100% humidity for 2 hours.

The incubated embryos were washed twice with the PBS working solution, then subjected to PBS removal through a three-step process, and equilibrated for 5 min in a freezing solution (Bioniche, ViGRO™, ETHYLENE GLYCOL FREEZE (with Sucrose), Lot:150206-2P). Afterwards, the embryos were placed in 0.25 ml plastic straws. Then the straws containing the embryos were placed in a control rate freezer, cooled to −5° C. at a rate of 1° C./min, and then equilibrated for 10 min. During equilibration, the straws containing the embryos were clamped with pre-cooled forceps at the upper end for 3-5 seconds, thereby the freezing solution forming ice crystals, that is to say, ice seeding was completed. The straws containing the embryos were equilibrated for another 10 minutes, and then cooled down to −35° C. at a rate of 0.3° C./min. Subsequently, the frozen straws were placed in liquid nitrogen.

During thawing, the frozen straws were removed from the liquid nitrogen, gently shaken at room temperature for 5-10 seconds, placed in water at 35° C. for 10-15 seconds, and then removed from the water. The plugs at both ends of the straws were cut off, and then the embryos in the straws were placed in watch glasses, and subjected to the removal of the freezing solution through a three-step process. After recovery by thawing, the embryos were placed into drops of equilibrated fresh CZB for 24-hour recovery. After 24 hours, the thawed recovery rate was counted.

The three-step process for PBS removal as mentioned above was specifically as follows. Before the embryos were immersed in the freezing solution and then placed in straws for freezing, they were washed with 100 µl of the drops of the following mixed solutions sequentially (3-5 min for each mixed solution): the freezing solution ⅓+PBS ⅔, the freezing solution ½+PBS ½, and the freezing solution ⅔+PBS ⅓.

The three-step process for the removal of the freezing solution as mentioned above was specifically as follows. The embryos were washed with 100 µl of the drops of the following mixed solutions sequentially (3-5 min for each mixed solution): the freezing solution ⅔+PBS ⅓, the freezing solution ½+PBS ½, and the freezing solution ⅓+PBS ⅔.

3. Data Analysis

All the experimental data was subjected to Chi-square analysis by SPSS 21.0 statistical software.

4. Results 4.1. Effect of Different Concentrations of E-64d in the Culture Medium on the Thawed Recovery Rate of Normally Hatched Blastocysts from Mice

TABLE 1 the thawed recovery rate (%) of normally hatched blastocysts incubated with different concentrations of E-64d

| E-64d concentration (µmol/L) | the thawed recovery rate (%) |
|---|---|
| 0 | 73.40 ± 4.30[B] |
| 0.5 | 75.35 ± 3.51[b] |
| 1 | 80.67 ± 5.40[4a] |
| 1.5 | 79.45 ± 4.28[4a] |
| 2 | 78.65 ± 2.56[b] |
| 3 | 76.26 ± 5.32[b] |
| 5 | 72.64 ± 2.13[B] |
| 10 | 62.58 ± 3.72[B] |

Note:
The values are expressed as mean ± standard deviation. For individual treatment groups, different uppercase letters indicate extremely significant difference (P < 0.01); and different lowercase letters indicate significant difference (P < 0.05); and no letters indicate no difference (P > 0.05). The experiments were repeated three times.

The above results show that, when the embryos are incubated in an E-64d-containing in-vitro embryo culture medium for a period of time prior to the embryo freezing, the thawed recovery rate of the embryos will be affected. It can be seen from Table 1 that, after the embryos are incubated in an in-vitro embryonic culture medium containing E-64d at low concentrations of, for example, 0.5-3 µmol/L, for a period of time, the thawed recovery rates of the embryos are improved to different extents as compared with the control.

Where the concentration is 1 or 1.5 µmol/L, the thawed recovery rate is improved by about 10%, which is most significant. However, E-64d at an even higher concentration hardly or even negatively affects the thawed recovery rate of the embryos. For example, when E-64d is at 5 µmol/L, the thawed recovery rate of embryos is nearly comparable to that in absence of the inhibitor. Moreover, when E-64d is at 10 µmol/L, there is even a negative effect, and the thawed recovery rate is decreased to 62.58%, by about 15% as compared with the control. It can be seen that incubation of normally hatched embryos in an in-vitro embryonic culture medium containing E-64d at a low concentration prior to the embryo freezing can significantly improve the thawed recovery rate of the embryos.

It will be apparent to those skilled in the art that the present invention is not limited to the details exemplified above. Variations can be made to the technical solutions described herein by those skilled in the art without departing from the spirit and principle of the present invention, and also fall within the protection scope as defined by the appended claims of the present invention.

In addition, it should be understood that although the present invention has been described by reference to embodiments herein, it is not the case that each embodiment includes only one independent technical solution. This way of description herein is merely for the sake of clarity, and the present description should be considered as a whole by those skilled in the art. The technical solutions provided in various embodiments can be suitably combined to form other embodiments that are comprehensible by those skilled in the art.

What is claimed is:

1. A method for improving the freezing resistance and the thawing recovery rate of an embryo, comprising incubating the embryo in an in-vitro embryonic culture medium comprising an inhibitor of Cathepsin L prior to embryo freezing, wherein the inhibitor of Cathepsin L is E-64d at a concentration of 0.5-3 µmol/L; the in-vitro embryonic culture medium is a CZB medium, and the embryo is derived from mouse.

2. The method for improving the freezing resistance and the thawing recovery rate of an embryo according to claim 1, wherein the E-64d is at a concentration of 0.5-2.0 µmol/L.

3. A method for freezing an embryo, comprising the steps of:
   a) incubating the embryo in an in-vitro embryonic culture medium comprising an inhibitor of Cathepsin L, wherein the inhibitor of Cathepsin L is E-64d at a concentration of 0.5-3 µmol/L; the in-vitro embryonic culture medium is a CZB medium, and the embryo is derived from mouse; and
   b) subjecting the embryo incubated in step a) to freezing.

4. The method for freezing an embryo according to claim 3, wherein the E-64d is at a concentration of 0.5-2.0 µmol/L.

5. The method for improving the freezing resistance and the thawing recovery rate of an embryo according to claim 1, wherein the embryo is incubated for 1-4 hours prior to embryo freezing.

6. The method for improving the freezing resistance and the thawing recovery rate of an embryo according to claim 1, wherein the embryo is incubated for 2 hours prior to embryo freezing.

7. The method for improving the freezing resistance and the thawing recovery rate of an embryo according to claim 2, wherein the E-64d is at a concentration of 1.0-1.5 µmol/L.

8. The method for improving the freezing resistance and the thawing recovery rate of an embryo according to claim 2, wherein the E-64d is at a concentration of 1 µmol/L.

9. The method for freezing an embryo according to claim 3, wherein the embryo is incubated in the in-vitro embryonic culture medium for 1-4 hours.

10. The method for freezing an embryo according to claim 3, wherein the embryo is incubated in the in-vitro embryonic culture medium for 2 hours.

11. The method for freezing an embryo according to claim 3, wherein the freezing is programmed freezing.

12. The method for freezing an embryo according to claim 4, wherein the E-64d is at a concentration of 1.0-1.5 µmol/L.

13. The method for freezing an embryo according to claim 4, wherein the E-64d is at a concentration of 1 µmol/L.

* * * * *